(12) United States Patent
Mark

(10) Patent No.: US 6,334,774 B1
(45) Date of Patent: Jan. 1, 2002

(54) FLOW THROUGH APPLICATOR WITH RESILIENT TIP

(76) Inventor: Phillip Mark, 1255 La Quinta Dr., #214A, Orlando, FL (US) 32809

( * ) Notice: Subject to any disclaimer, the term of this patent is extended or adjusted under 35 U.S.C. 154(b) by 0 days.

(21) Appl. No.: 09/718,379

(22) Filed: Nov. 24, 2000

(51) Int. Cl.$^7$ ................................................. A61C 5/04
(52) U.S. Cl. ........................................ 433/89; 401/265
(58) Field of Search ............................. 433/89, 90, 80, 433/82, 163, 164; 604/310; 401/265, 266; 601/163, 162; 222/568, 567

(56) References Cited

U.S. PATENT DOCUMENTS

| | | |
|---|---|---|
| 3,086,249 A | 4/1963 | Nelson et al. |
| 3,115,682 A | 12/1963 | Soubier et al. |
| 3,144,493 A | 8/1964 | Santelli |
| 3,341,043 A | 9/1967 | Santelli |
| 3,558,751 A | 1/1971 | Santelli |
| 4,293,520 A | 10/1981 | Akutsu ........................ 264/513 |
| 4,507,258 A | 3/1985 | Aoki ........................... 264/255 |
| 4,715,504 A | 12/1987 | Chang et al. ................... 215/1 |
| 4,909,416 A * | 3/1990 | Evezich ........................ 222/95 |
| 4,990,301 A | 2/1991 | Krishnakumar et al. ..... 264/513 |
| 5,098,291 A * | 3/1992 | Curtis et al. ................... 433/89 |
| 5,626,473 A * | 5/1997 | Muhlbauer .................... 433/89 |
| 5,792,397 A | 8/1998 | Ritchey ..................... 264/40.7 |
| 5,829,976 A * | 11/1998 | Green .......................... 433/89 |
| 5,897,822 A | 4/1999 | van Manen et al. ......... 264/255 |
| 6,062,841 A | 5/2000 | Gellert et al. ............... 425/130 |

* cited by examiner

Primary Examiner—John J. Wilson
Assistant Examiner—Melba Bumgarner
(74) Attorney, Agent, or Firm—Eric P. Schellin

(57) ABSTRACT

A fluid applicator which is constructed of a relatively rigid plastic with a forwardly disposed distal end portion or nozzle which is constructed of a plastic material which is relatively more resilient. The applicator in some embodiments being adapted and constructed to be affixed to a syringe containing a to-be-distributed relatively high viscosity liquid or gel.

1 Claim, 4 Drawing Sheets

FLOW THROUGH APPLICATOR WITH RESILIENT TIP

BACKGROUND OF THE INVENTION

Flow through applicators have become a well accepted part of dentistry. Such applicators are usually operatively affixed to a source of liquid or gel material. The source usually has means for pressurizing the liquid-gel into and through the applicator. In many instances the source may be a loaded syringe On the other hand the source may be the applicator itself which may have a proximate chamber for containing a liquid. The chamber is fitted with a piston plug for driving the liquid out of the applicator.

In many instances the distal end of the applicator is fitted with bristles so that the liquid or gel flowing from the applicator can be distributed as by brushing back and forth for instance. Such bristles frequently overlap the bore out of which the liquid or gel is being expressed and thereby hinders the clear flow capability.

When no bristles are present the end of the applicator tube is too rigid for affecting good distribution when the distal tip of the applicator is used as a manually employed wiping distributor. If the applicator is constructed of a very resilient or flexible plastic good distribution can be obtained but the structure of the applicable does not have sufficient structurally integrity.

SUMMARY OF THE INVENTION

The present invention combines the use of a relatively hard or relatively rigid plastic for the main or major portion of the applicator with a less rigid or resilient plastic for the distal end of the applicator.

In the best mode the plastic parts are extruded consecutively so that the major portion of the applicator is extruded followed by the extrusion of the minor part, that is, the distal end.

In the preferred embodiment of fabrication, the applicator of the present invention is injection molded. It is begun by first loading the mold to produce the major part of the applicator followed by injecting the more resilient portion. It is also considered that the reverse may be contemplated where the minor portion may first be injected into the mold followed by injecting the more rigid plastic major portion. The less rigid plastic may be of a foam plastic material, preferably of a closed cell nature.

The concept of producing composite articles is already well known and can be seen in such patents as U.S. Pat. Nos. 3,086,249; 3,115,682; 3,558,751; 3,341,043; 4,293,520; 4,507,258; 4,715,504; 4,990,301; 5,792,397; 5,897,822 and 6,062,841. These patents are incorporated herein in their entireties by reference.

It is contemplated that the plastic materials applicable are well known. The selection is predicated on the major portion being rigid and having integrity and the resilient part being sufficiently soft and flexible to assist in the spreading and distribution. Applicable polymers are PVC, hard/soft; polycarbonate, ABS; ABS/polycarbonate alloys, acrylic, nylon 6.6 and various rubbers.

DETAILED DESCRIPTION OF THE DRAWINGS

Figure 1:
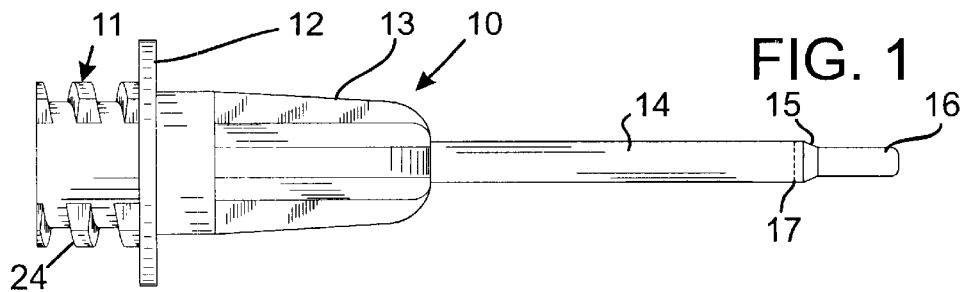
FIG. 1 is a side view of one embodiment of the applicator.

The applicator of the present invention is shown, generally, by reference numeral 10. It consists of a number of portions. A male threaded portion 11 is at its proximate end. Then, progressing from the proximate to the distal end, the threaded portion 11 terminates in a radially extending flange 12. The next portion is finger grip hub 13. The finger grip hub 13 has a series of four equi-spaced longitudinal radially extending flanges. The finger grip hub 13 has extending therefrom an elongated tube 14. The elongated tub terminates in a shoulder 15. Distally longitudinally extending from the shoulder 15 is a relatively shorter tube 16 of somewhat smaller external diameter than tube 14.

Demarcation line 17 of tube 14 is depicted to show that the material distally beyond is of a plastic material having relatively considerably more resiliency than the plastic material extending proximately of said line of demarcation. Although it is contemplated that the main portion may be constructed of metal and the more resilient portion of plastic.

Figure 2:
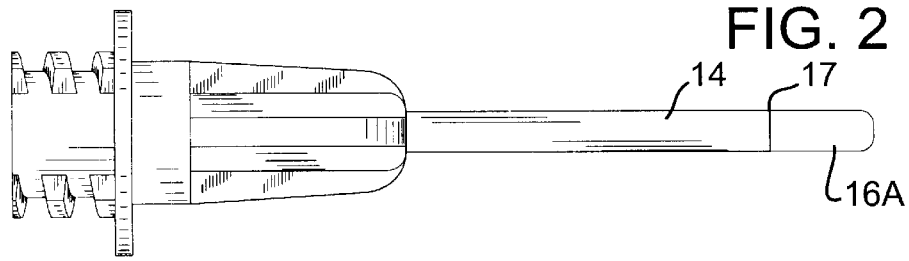
FIG. 2 is a side view of second embodiment of the applicator.

In FIG. 2, the line of demarcation 17 separates the tube 14 from a distal tube 16A which is essentially like tube 16 but tube 16A does not have a shoulder 15 nor is of smaller diameter than tube 14.

Figure 3:
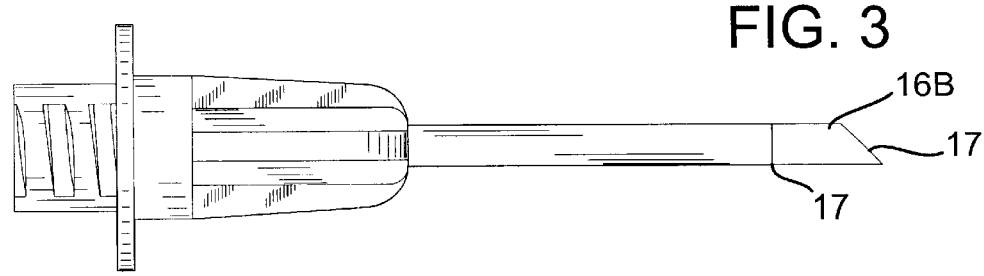
FIG. 3 is a side view of a third embodiment of the applicator.

FIG. 3 is a third embodiment, which is like FIG. 2 except for at distal end 16B which is bevelled at plane 17.

Figure 4:
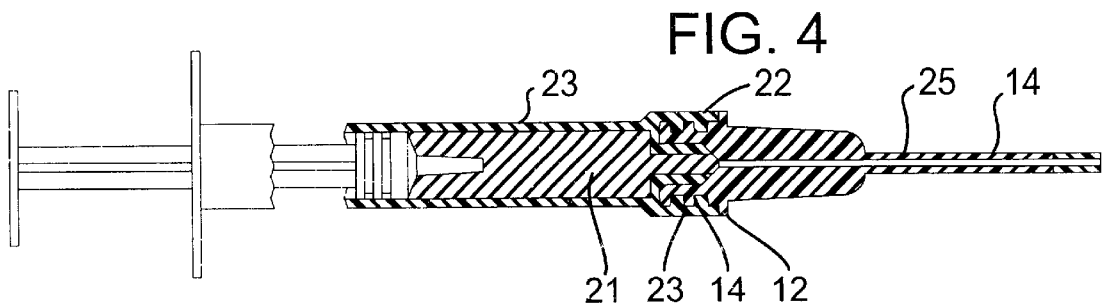
FIG. 4 is partial fragmentary and partial linear cross-section of the applicator with a syringe attached thereto.

FIG. 4 is a cross section view with the applicator 10 being secured to a conventional syringe 20 which is loaded with gel material 21. The distal part 22 of the syringe 20 is a female portion being threaded on the inside of a cylinder to cooperate with thread 24 on the male portion 17. The cylinder 23 abuts against flange 12. The finger grip portion 13, the tube 14 and the distal tube 16B all have an interconnecting bore 25.

Figure 5:
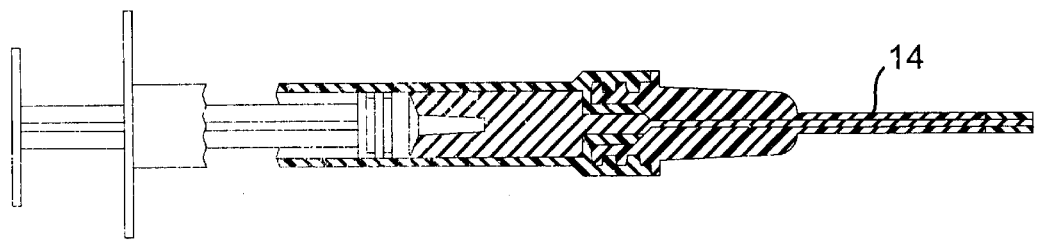
FIG. 5 is a partial fragmentary and partial linear cross-section of another embodiment of the applicator with a syringe attached thereto.

In FIG. 5 a portion of the gel 21 in the syringe is shown to be expressed from the tube 14.

Figure 6:
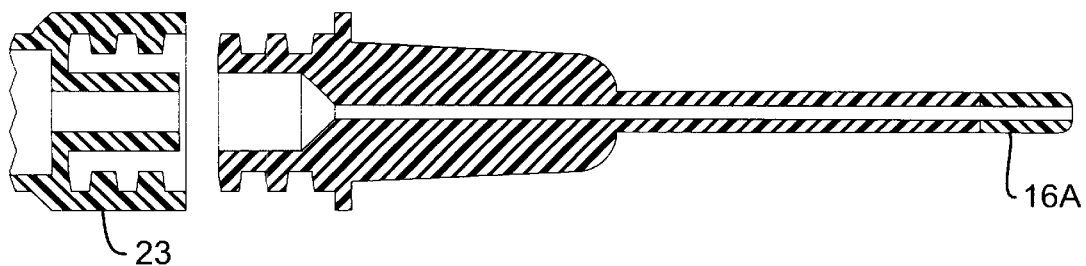
FIG. 6 is a cross-section of the applicator of FIG. 2 with a fragmentary and partial view of the syringe.

FIG. 6 depicts the applicator with a cross-sectioned view in fragmentary condition of the cylinder 23 as it approaches a confronting relationship, leading to a screwing on of the syringe onto the applicator.

Figure 7:
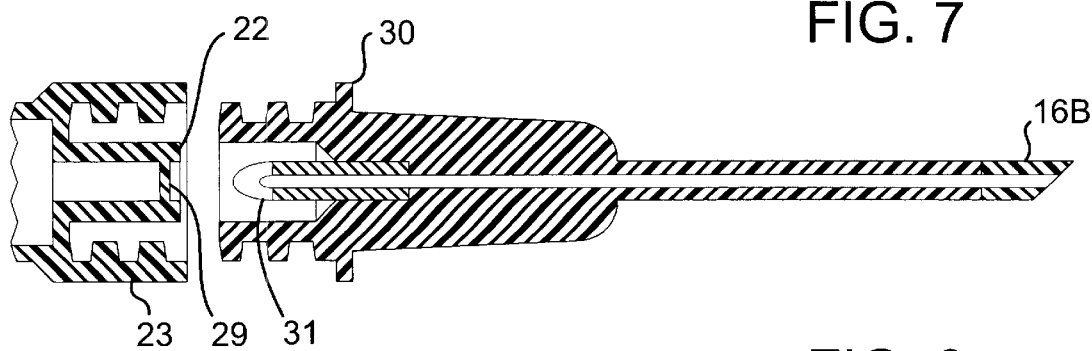
FIG. 7 is a cross-section of the applicator of FIG. 3 with a fragmentary and partial view of the syringe.

In FIG. 7 the cylinder 23 of the syringe is shown to have an inner concentric tube 28 which has a membrane 29 which is pierced by a spike 30 concentrically positioned in the male portion 17 of the applicator of the present invention. The forward portion 31 penetrates through membrane 29 whereby the contents of the syringe may be expressed into and through the applicator which in the embodiment shown terminates in a bevelled portion 16B.

Figure 8:
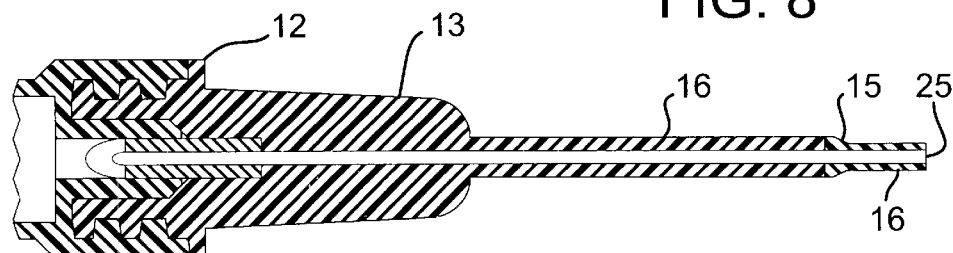
FIG. 8 is a cross-section of the applicator of FIG. 1 with a fragmentary syringe and in cross-section.

FIG. 8 shows the cylinder 23 of the syringe of FIG. 7 in screwed on position against flange 12.

Figure 11:
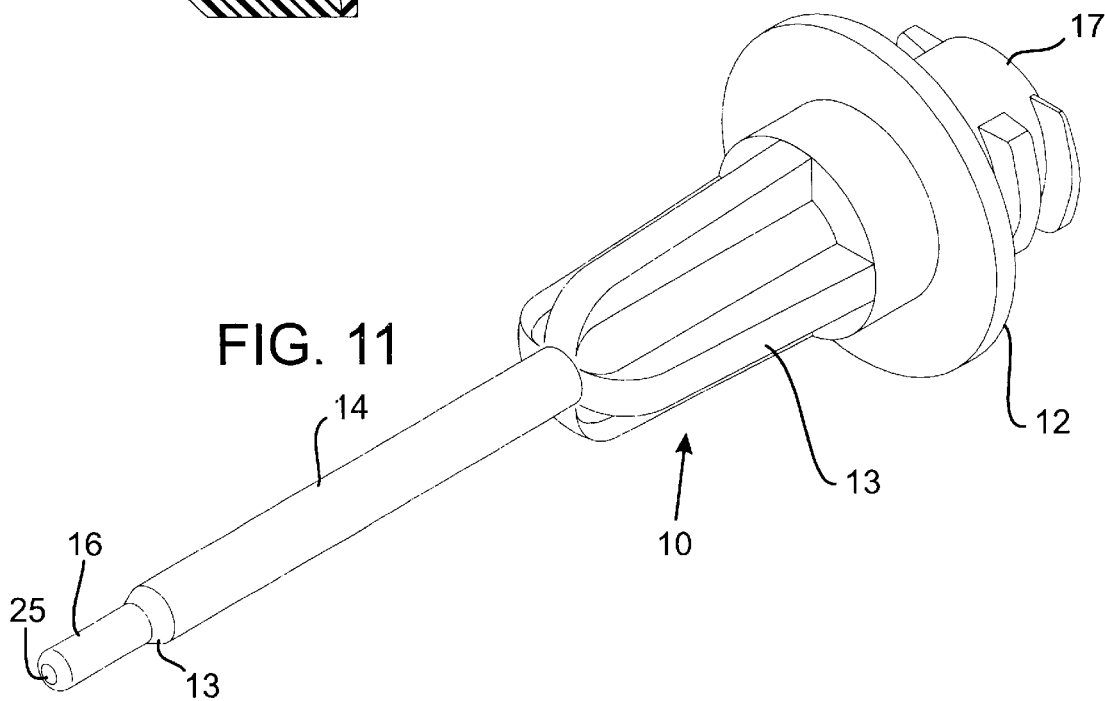
FIG. 11 is a perspective view of the applicator of FIG. 1.

FIG. 11 is the applicator of FIG. 1 presenting a clear view of the applicator of the present invention.

Figure 9:
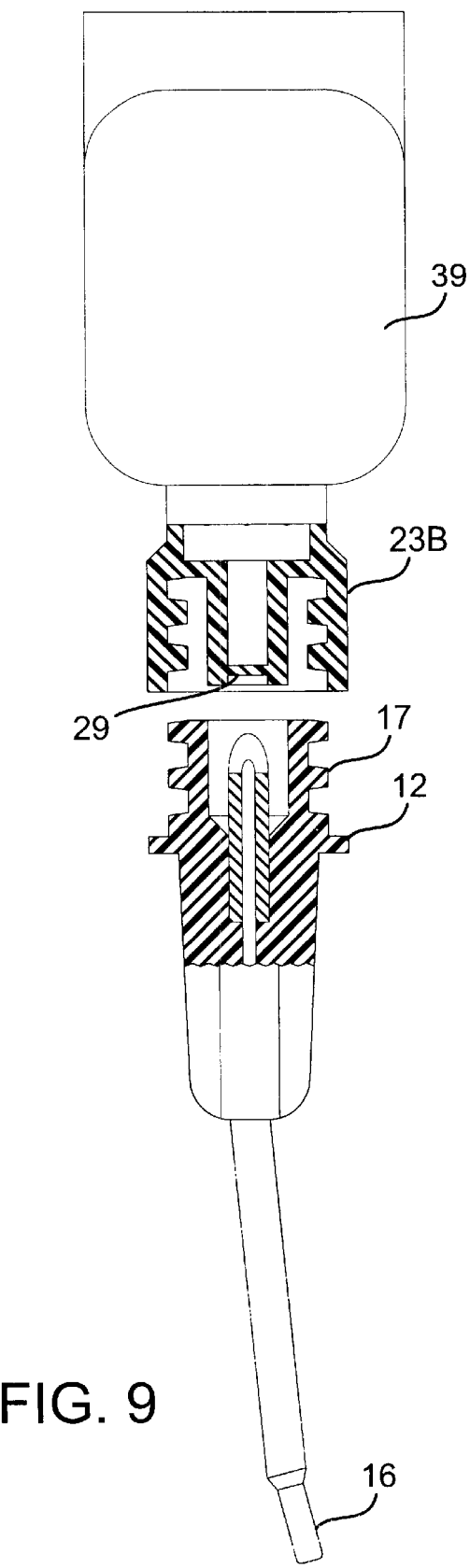
FIG. 9 is a side view of another embodiment of the applicator with a partial thereof being in cross-section.
Figure 10:
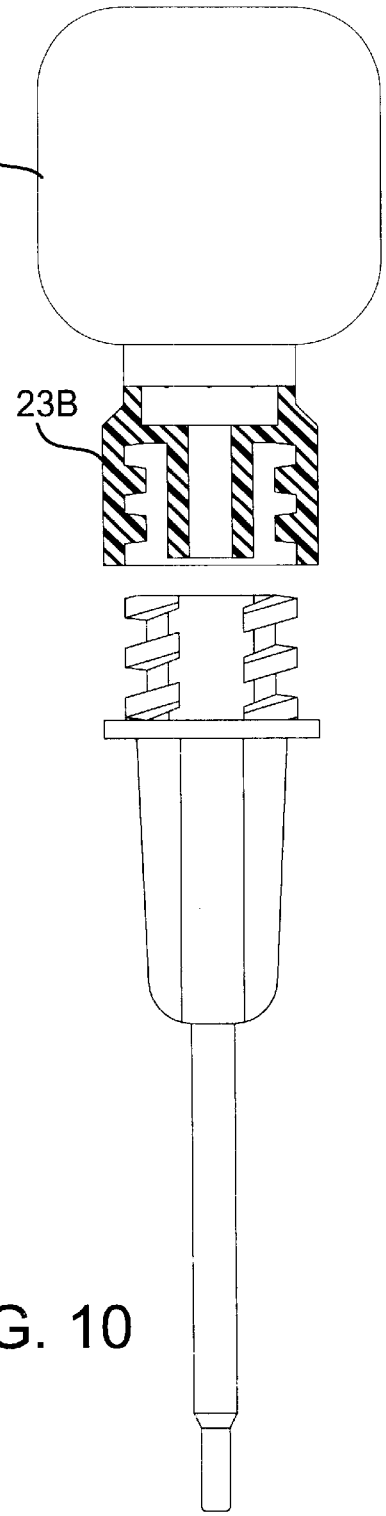
FIG. 10 is a side view of still another embodiment of the applicator with a compressible bulb.

FIGS. 9 and 10 depict a more radical departure of the present invention wherein instead of employing a syringe, the cylinder 23 is either cylinder 23A in FIG. 9 or cylinder 23B of FIG. 10. In both instances the cylinder is part of a compressible bulb 39. In FIG. 10 the set up does not include a pierceable membrane 29 so that when the bulb 30 is screwed on to threaded male portion 17 a deflection of the bulb will express the gel contents in the bulb 39 therefrom and through bore 25.

FIG. 9, the membrane 29 must first be pierced by spike 30, followed by screwing onto male portion 17 of the applicator, and then followed by squeezing the bulb 39 to express the gel material. In this embodiment it will be seen that the distal portion 16 is at an acute angle. This has been found desirable in some instances of application.

Figure 12:
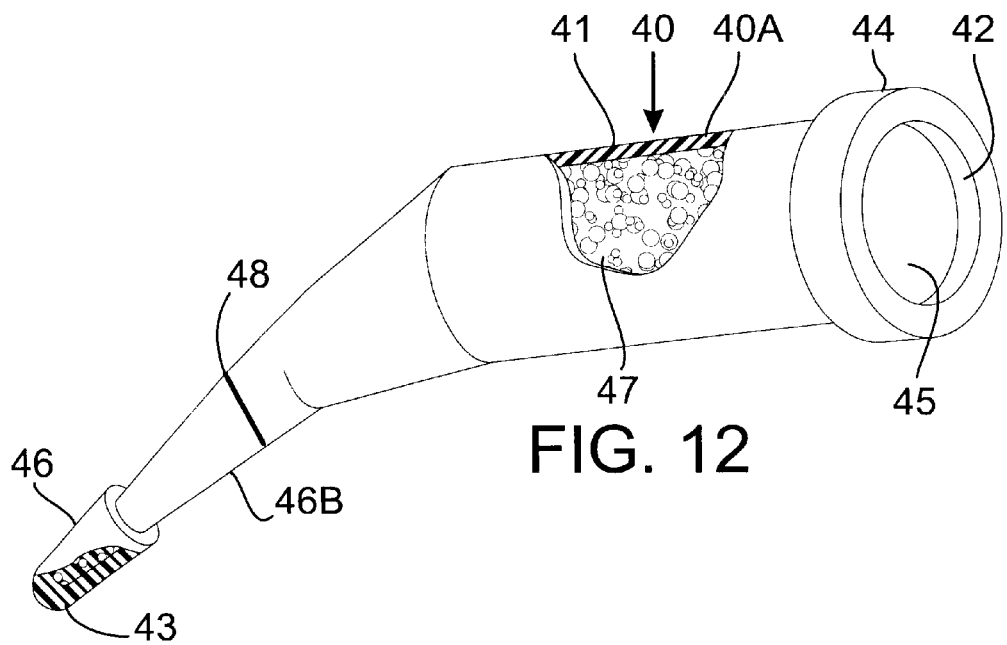
FIG. 12 is a side elevation view of a dental capsule embodying the invention and having portions thereof broken away.

Referring to the drawings, there is shown in FIG. 12 a capsule 40 which depicts another embodiment of the present invention. As shown the capsule 40 has a body portion 40A defining a chamber or reservoir 41 that is open at one end as indicated at 42. In the illustrated embodiment of FIG. 12, a discharge nozzle 40B is connected to the other end of the reservoir or chamber 41 that tapers inwardly toward the discharge orifice 43. The entire nozzle 40B may be of a plastic less rigid than the body portion 40A which is more rigid. It is also contemplated that only a distal portion of the nozzle 40B may be constructed of a resilient plastic. When the differences of plastic is sharply defined there will be a defined demarcation line 48. If the area of change is gradual there will be no line of demarcation. A laterally outwardly extending flange 44 circumscribes the open end of the capsule body portion 40A. In the assembled form of the capsule as seen in FIG. 12 a displaceable piston 45 is fitted into the open end 42 to seal the open end 42. While the described capsule 40 is illustrated as having a specific geometric shape, it will be understood that the specific shape or size of the capsule is not critical to the invention, as the capsule may assume any of the shapes or size that are disclosed in patents known to those skilled in the art. The invention to be described would be operative in any dental capsule that includes a body portion defining a chamber that is opened at one end and has a discharge nozzle connected to the other end and which open end is adapted to be sealed by a displaceable piston.

In accordance with this invention, a gel 47, is charged into a body portion 40A or reservoir 41. The filler 47 is saturated with a dental fluent low viscosity or liquid-like material. The open end 42 of the capsule 40 is then sealed by inserting therein a displaceable piston 45. If desired, the discharge orifice 43 may be sealed by a sealing cap 46 to protect the contents of the capsule from any contaminants such as dirt, dust and to prevent evaporation or drying of the gel 47.

To dispense gel 47, the capsule 40 is placed in a suitable syringe. With the sealing cap 46 removed and upon the actuation of the syringe (not shown), the piston 45 is displaced so as to impart a compressive force onto the gel 47, causing the gel contained therein to be squeezed out and dispensed through the discharge orifice 43. The amount of compressive force imparted by the piston 45 by the syringe and onto the gel 47 determines the amount of gel that is dispensed. Thus, it will be apparent that the user can readily control the dispensing of the gel by regulating the amount of force that is applied by the piston 45 onto the filler.

Figure 13:
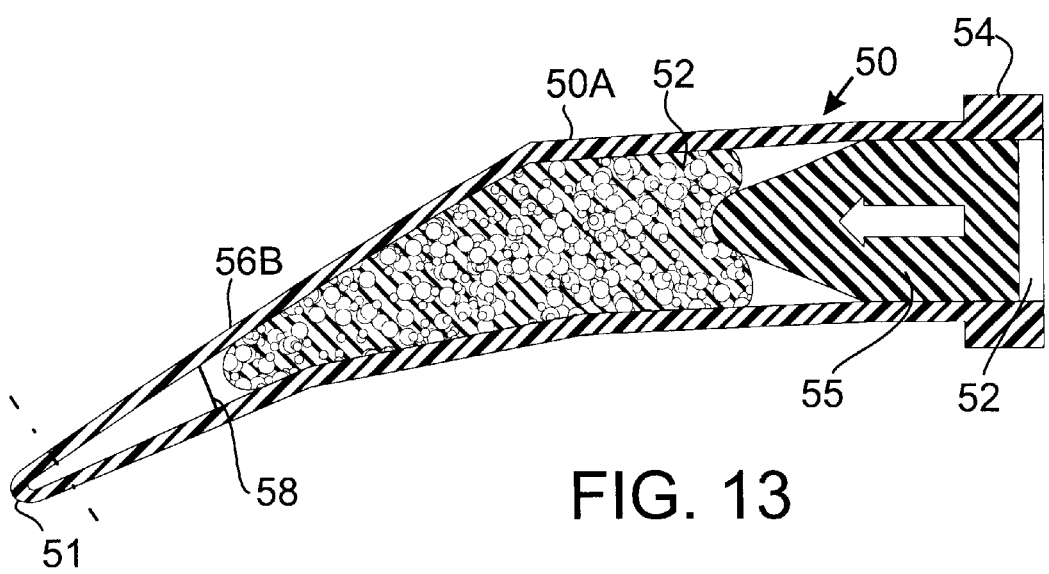
FIG. 13 is a sectional side view of FIG. 12 with some modification.

FIG. 13 illustrates a slightly modified form of the invention. In this embodiment, the capsule 50 is virtually identical to that described with respect to FIG. 12 except the end of the discharge nozzle 50B is initially sealed as indicated at 51 in the molding of the capsule 50. In all other respects, capsule the molding of the capsule 50. In all other respects, capsule 50 is identical to that described with respect to the embodiment of FIG. 12. That is, the capsule 50 includes a body portion 50A having an open end 52 circumscribed by a flange 54 and a piston 55 for sealing the open end 52. Disposed within the body or reservoir 51 is a filler 57 saturated with a low viscosity dental material similar to that hereinbefore described. Again the distal part will be fabricated of a resilient plastic, i.e. of less rigid plastic than the major portion. So when the change of plastic is abrupt line 58 is a line of demarcation.

To dispense the liquid or fluent material, the dentist or user must first cut off the sealed end 51 of capsule 50 to form the discharge orifice. In all other respects, the operation of capsule 50 is similar to the hereinbefore described. Although, it can be available open or closed. As necessary additional information can be obtained from a review of the prior art embodied in U.S. Pat. No. 6,099,307, which is incorporated herein in its entirety by reference.

In all instances the applicator is constructed of a plastic material of relative rigidity. Furthermore, in all instances of the present invention the distal portion 16, 16A and 16B is constructed of a plastic that is less rigid and has greater resiliency so that the applicator may be stroked back and forth to distribute the expressed gel in a wiping or painting manner. The differences between the plastic of the main or major portion of the applicator and the minor portion of the applicator makes it possible to achieve the desirable results of good distribution on a receiving surface.

What is claimed is:

1. A liquid flow through injection molded thermoplastic applicator comprising a main body and a minor body, the main body having a threaded proximate end, said proximate end terminating distally in a radially extending flange on one side thereof, a finger grip portion on the other side of said flange, a distal end of said grip portion having an elongated tube attached thereto, said tube terminating in a rigid thermoplastic distal tube, said distal tube in turn terminating in said minor body comprising a less rigid thermoplastic foamed material integral and coextensive with said rigid thermoplastic distal tube, said main body and said minor body being sequentially injection molded.

* * * * *